(12) United States Patent
West et al.

(10) Patent No.: US 8,603,307 B2
(45) Date of Patent: Dec. 10, 2013

(54) SELF-DIAGNOSTIC SENSOR SYSTEM

(75) Inventors: Steven J. West, Hull, MA (US); Timothy C. Gillette, Brookline, MA (US)

(73) Assignee: Thermo Fisher Scientific, Inc., Beverly, MA (US)

( * ) Notice: Subject to any disclaimer, the term of this patent is extended or adjusted under 35 U.S.C. 154(b) by 1107 days.

(21) Appl. No.: 12/127,534

(22) Filed: May 27, 2008

(65) Prior Publication Data

US 2008/0289959 A1    Nov. 27, 2008

Related U.S. Application Data

(60) Provisional application No. 60/940,208, filed on May 25, 2007.

(51) Int. Cl.
 *G01N 27/333* (2006.01)
 *G01N 27/36* (2006.01)
(52) U.S. Cl.
 USPC ............................ 204/401; 204/406; 204/416
(58) Field of Classification Search
 USPC ........................ 204/400–435; 205/775–794.5; 600/345–348; 324/438
 See application file for complete search history.

(56) References Cited

U.S. PATENT DOCUMENTS

| | | | | |
|---|---|---|---|---|
| 5,897,522 A | * | 4/1999 | Nitzan | 604/20 |
| 6,740,216 B2 | * | 5/2004 | Diakonov et al. | 204/418 |
| 7,076,399 B2 | * | 7/2006 | Godara | 702/183 |
| 2003/0020478 A1 | * | 1/2003 | Scott | 324/426 |

FOREIGN PATENT DOCUMENTS

| | | | |
|---|---|---|---|
| JP | 53147594 A | * | 12/1978 |
| WO | WO 9918430 A1 | * | 4/1999 |

OTHER PUBLICATIONS

SUGAWARA—JP53147594 A, 1978 English equiv of abstract.*

* cited by examiner

*Primary Examiner* — Susan D Leong
(74) *Attorney, Agent, or Firm* — Cesari and McKenna, LLP

(57) ABSTRACT

A system for monitoring the viability of an electrochemical cell measures the impedance of the cell over a wide range of impedances and with diminished phase shift over prior methods so that a more nearly accurate assessment of the impedance can be made. The system is particularly useful for four electrode systems, but is not so limited. It may advantageously be incorporated in the cell itself to further minimize cabling artifacts.

7 Claims, 2 Drawing Sheets

SELF-DIAGNOSTIC SENSOR SYSTEM

CROSS-REFERENCE TO RELATED APPLICATIONS

The present application claims the benefit of U.S. Provisional Patent Application Ser. No. 60/940,208 which was filed on May 25, 2007, by Steven J. West for Self-Diagnostic Sensor System and is hereby incorporated by reference.

BACKGROUND OF THE INVENTION

1. Field of the Invention

The invention relates to electrochemical sensor systems, and comprises method and apparatus for monitoring and diagnosing the operation of such systems.

2. Background Information

It is desirable to be able to assess the "health" of a sensor that is being used to deliver information about a sample or process under test. The definition of health could be as simple as "broken" or "not broken" in the case of a glass-membrane pH sensor, or might be expanded to include qualitative or quantitative assessments of the functional performance of specific parts of the sensor as a system, for example, the impedance of the glass membrane, impedance of the reference half-cell liquid junction, or other parameter indicative of age or wear.

SUMMARY OF THE INVENTION

The present invention is a sensor for monitoring the viability of an electrochemical cell. Although the sensor may contain elements that facilitate the transfer of normally expected information—for example, a pH signal in the case of a pH electrode—its main purpose is to interrogate the sensor for information that is indicative of the sensor's health. A key capability of this sensor is to apply an AC voltage signal across two elements of the sensor, the frequency of which signal varies according to a prescribed program, and to read back an impedance spectrum, that is, an array of data consisting of the real and imaginary components of the impedance as a function of frequency, and or the phase angle of the resultant current signal as a function of frequency. This data is then communicated to a processing unit which may also be part of the embedded circuit, or may reside in a separate processing unit such as a pH meter, other meter, or computer. The communication may occur through a cable or by means of a RF transceiver, also part of the embedded circuit, and a corresponding transceiver in the processing unit. (For purposes of explanation, the discussion will focus on the impedance spectrum, although it will be understood by those skilled in the art that, alternatively, one may generate the admittance spectrum for the same purpose. Use of the term "impedance" should thus be understood as encompassing both.)

For example, a combination pH sensor used for the monitoring of industrial processes usually consists of three electrodes in contact with a test medium: a sensing electrode, usually a wire and electrolyte in a pH-sensitive glass bulb; a reference electrode consisting of a wire and electrolyte contacting the medium through a restrictive liquid junction; and a solution ground, usually an inert metal pin. The glass bulb has a characteristic resistance, which normally increases with age or may decrease if cracked or broken. Therefore, knowledge of this resistance is useful diagnostically. Determining this resistance is complicated by the fact that the bulb has capacitive impedance that must be distinguished from the resistive impedance. An impedance spectrum, taken between the solution ground and the wire in the glass bulb, provides detailed information about the complex impedance of the glass bulb, allowing the diagnostically important resistive component of the impedance to be determined. Likewise, the resistance of the liquid junction is diagnostic of its health. Exhaustion of electrolyte or clogging can be indicated by interrogating the junction with IS between the reference wire and solution ground.

A related example of the utility of this technique can be found in the case of a sodium ion-selective electrode (ISE). Like a pH electrode, this is also a glass electrode. In the case of sodium, however, the increase in bulb resistance with time is much greater and degrades its response time to changes in sodium. The resistance and therefore response time can be restored, however, by etching with hydrofluoric acid. IS (impedance spectroscopy) can be used to indicate when the electrode needs to be etched.

One disadvantage of current systems for impedance spectroscopy is that the cabling to the electrochemical cell being monitored can introduce substantial attenuation and/or phase shift. In accordance with one embodiment of the present invention, this error source is eliminated by forming the sensor integral with the cell, i.e., either within the cell itself or attached to the cell, so that the impedance measurements are obtained without having to traverse the cabling that connects the cell to a measuring instrument. An example of an impedance analyzer that is small enough to be embedded within the normal envelope of a sensor such as a pH sensor is the Model AD5934 Impedance Converter/Network Analyzer from Analog Devices, Norwood, Mass. Such a chip is particularly useful in connection with the practice of the present invention, although the invention is not limited to its use.

There is another benefit to having IS capability embedded in a pH electrode. U.S. Pat. Nos. 4,321,544 and 6,168,707 describe a means of determining the temperature of a pH measurement through measurement of the resistance of the glass membrane, which depends on temperature. In the systems described in U.S. Pat. Nos. 4,321,544 and 6,168,707, however, a single very low frequency signal (~5 Hz) is applied. The frequency must be low in order to reduce capacitive coupling in the electrode cable. The present invention, while not primarily directed at determination of glass membrane temperature, provides as a side benefit the capability to do so. Moreover, by being embedded in the electrode the limitation imposed by cabling is eliminated.

Dissolved oxygen (DO) electrodes can benefit from impedance analysis as well. Currently, some DO electrodes monitor the DC resistance across the gas-permeable membrane that separates the internal electrolyte from the test sample, in order to detect leaks. IS is a more powerful tool. The electrolyte/membrane/sample configuration in a DO electrode is very similar to a parallel-plate capacitor where the membrane thickness determines the distance between the plates. Interrogation of this system by IS may yield information not only about leaks but about membrane thickness and fouling as well.

One of the most useful electrochemical sensor systems where impedance spectroscopy can be applied is electrolytic conductivity. Today, conductivity meters often are capable of applying several frequencies to a conductivity cell in order to get as wide a linear measurement range as possible. Having several frequencies allows measurements to be made over a wide range while keeping the phase angle at a minimum, so that the purely resistive component of the impedance is used to calculate conductivity. With the practical continuum of frequencies applied in IS, phase angle can be continuously monitored to optimize readings for minimum phase angle. In addition, some conductivity cell electrodes can become fouled or inactivated over time. IS provides the means to detect fouling or inactivation. When it reaches the point that satisfactorily low phase angle cannot be achieved at any frequency, the instrumentation can notify the user that electrode maintenance is required. And, as mentioned above, having the IS circuitry embedded in the probe eliminates limitations imposed by cabling.

In another embodiment of the invention, a self-diagnostic sensor system for monitoring the viability of a four cell conductivity electrode is described. By measuring the amplitude and phase of a conductivity electrode over a wide frequency range (for example, from 30 Hz to 100,000 Hz), the frequency or frequency ranges that have the most consistent magnitude and lowest phase angle can then be selected for establishing the conductivity. Since the sense electrodes and drive electrodes are separate in such an electrode, the difference in the amplitude and phase of the voltages at the respective terminal pairs that are inherent in conventional techniques would introduce serious errors in the determination of impedance. This has heretofore limited the use of impedance spectroscopy to two cell electrodes. This system may advantageously be positioned integral with the cell as discussed above, but may also be positioned remote from the cell, e.g., in a measuring instrument connected to the cell by a cable, without suffering the disadvantages of prior cabled systems.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
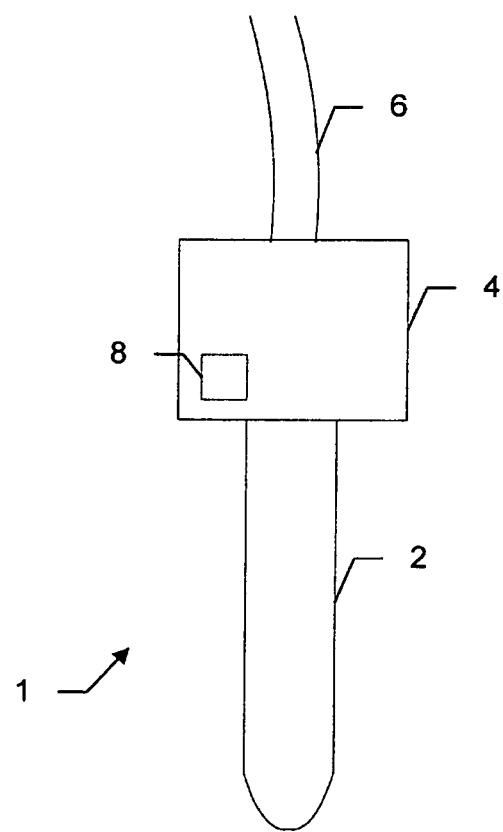
FIG. 1 is views in perspective of an electrochemical electrode in accordance with the present invention.

In FIG. 1, an electrochemical cell 1 such as an ion-specific electrode (ISE), a conductance cell, or the like has a body 2 for immersion in a solution, one or more of whose characteristics is being measured, and a cap 4 to which a cable 6 is connected. The cable provides power and measuring signals to the cell and receives signals from it. A chip 8 in cap 6 contains sensor circuitry in accordance with the one aspect of the present invention for monitoring the viability of the cell and for additionally providing an alarm when that viability is impaired. As noted above, the Analog Devices Model AD5934 Impedance Converter/Network Analyzer is a particularly suitable device for this purpose, since it contains, inter alia, a sine wave generator for generating the necessary drive signals, as well as circuitry for mathematically operating on the signals received from the cell in response to the drive signals to thereby generate digital outputs providing the magnitude and phase of the impedance over a broad range of frequencies. However, it will be understood that this embodiment is not limited to that circuit, and other circuitry performing the same functions (such as discrete logic circuitry, programmable logic circuitry, microprocessors, and the like) may also be used.

Figure 2:
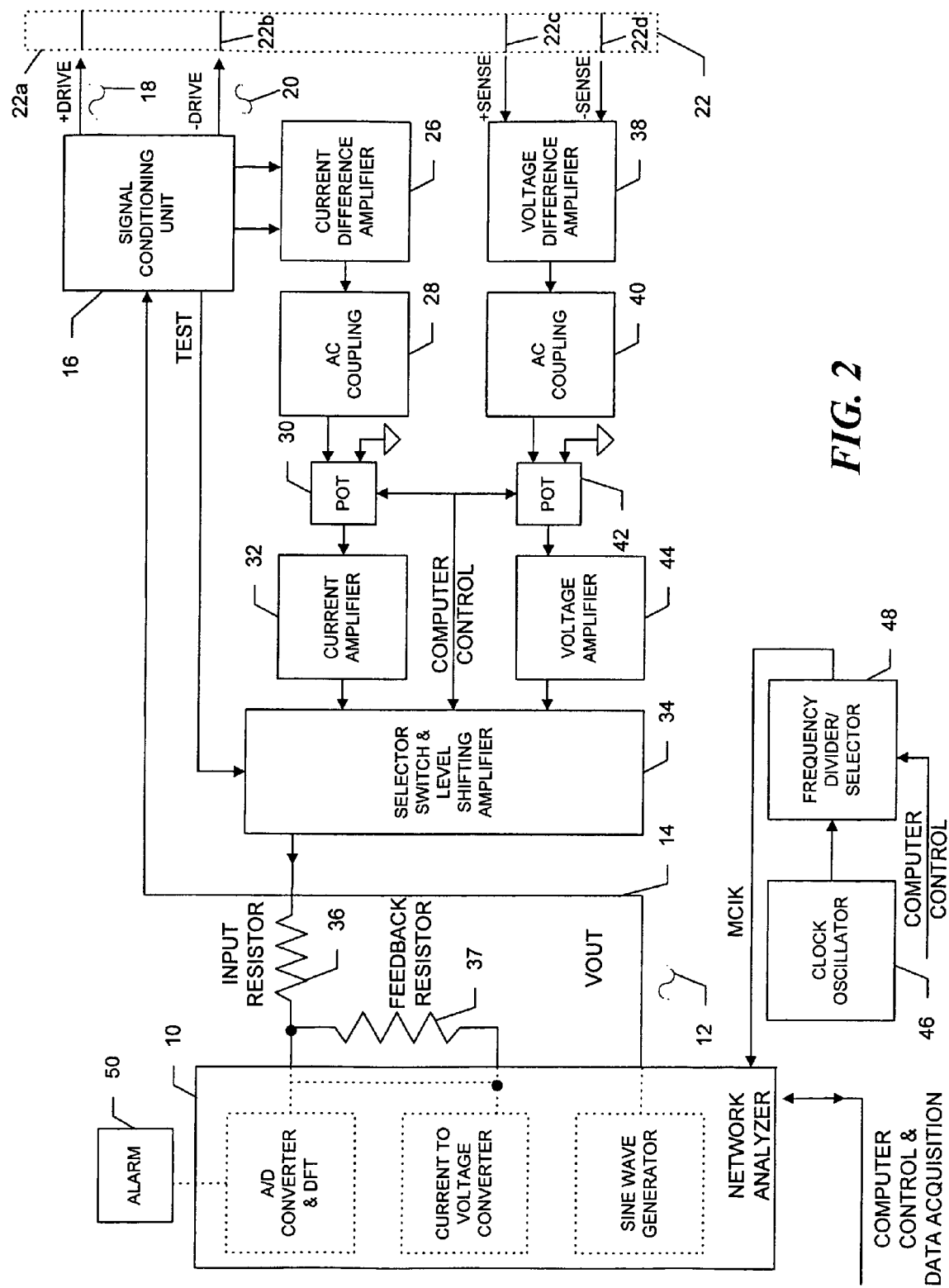
FIG. 2 is a block diagram of a specific embodiment of the invention as applied to measuring the impedance of a four cell electrode such as a four cell conductivity electrode.

Turning now to FIG. 2, a sensor for monitoring a four electrode cell, particularly a conductance cell, is shown in detail. This sensor circuit may be formed integral with the cell, as shown in FIG. 1, or it may be remote from the cell and connected to it by conductive leads, by wireless, or the like. In FIG. 2, a chip 10 provides a first drive signal 12 over a lead 14 to a signal conditioning unit 16. The drive signal is at a controlled amplitude or amplitudes and sweeps over a broad frequency range, e.g. on the order of 30 Hz to 100,000 Hz or more. Conditioning unit 16 is AC coupled to the drive signal 12 so as to remove any DC component in it, and generates a pair of complementary cell drive signals 18, 20 of defined amplitude that are respectively in phase with, and 180 degrees out of phase with, the drive signal 12. These are applied to a first pair of electrodes 22a, 22b of an electrochemical cell 22, such as a four cell conductivity cell.

In the embodiment described herein, the chip 10 was an Analog Devices® AD5934 Network Analyzer chip that generated a sine wave of amplitude two volts peak to peak over the indicated frequency range. The signal conditioning unit 16 was formed from a pair of inverting amplifiers, each of which provided an output voltage of one volt, peak to peak, so that the maximum voltage applied to the cell was two volts peak to peak. Current limiting resistors at the outputs of these amplifiers limited the current applied to the cell 22 to two milliamperes so as to minimize electrochemical interference.

The magnitude of the current being applied to the cell 22 is monitored by means of a current difference amplifier 26 which references the current to ground. The output of the amplifier 26 is then AC coupled (block 28) to a computer-controlled potentiometer 30 whose output is supplied through an amplifier 32 to a selector switch and level shifting amplifier 34. The AC coupling may simply comprise a capacitor or more elaborate coupling may be used. The output of the switch and amplifier 34 is applied through an input resistor 36 to a current-to-voltage converter section 10b of the analyzer 10. An analyzer portion 10c provides a digital measurement of the magnitude and phase of the input to the Analyzer.

In similar fashion the voltage across a second pair of electrodes of the cell, 22c, 22d, which serve as sensing electrodes, are applied to a voltage difference amplifier 38 which references the voltage to ground. The output of the amplifier 38 is then AC coupled (block 40) to a computer-controlled potentiometer 42 whose output is supplied through an amplifier 44 to the selector switch and level shifting amplifier 34. An oscillator 46 and a frequency divider 48 provide a master clock for drive signal generation by the Analyzer.

The selector switch and level shifting amplifier 34 performs two principal functions. First, it shifts the level of the signals applied to it to a range compatible with the Network Analyzer. Second, in response to control signals applied to it, it selectively switches its inputs between the current amplifier 32 and the voltage amplifier 34 so that the Analyzer can measure both the current applied to cell 22 and the response of the cell to that current.

As indicated, the operation of the Analyzer, the selection of driving frequencies, and the switching of level shifter and amplifier 34 are preferably performed responsive to a control program which steps the drive applied to the cell being tested across a range of frequencies to thereby enable determination of the impedance spectrum of the instrument being tested or monitored. Such a program is readily written by one skilled in the art.

In use, the impedance of a cell over a wide range of frequencies is determined by measuring the voltage generated at the sensing electrodes in response to the current measured at the drive electrodes. The ratio v/i of the voltage to the current defines the impedance of the cell, and the reciprocal i/v its conductivity. The voltage and the current are complex quantities, $v = v_r + j\, v_i$, and $i = i_r + j\, i_i$, where $v_r$ is the real part of the voltage, $v_i$ the imaginary part and j is the complex operator $(-1)^{1/2}$, and similarly for the current i. By measuring the current and voltage over a wide range of frequencies, one can usually find a range or ranges of frequencies over which the magnitude is relatively constant and the phase is at a minimum. The measurements made at these frequencies will provide the most nearly accurate conductivity measurement for the cell.

When the impedance measurements indicate that one or more if the real or imaginary parts of the measurements are varying excessively over the spectrum or are exceeding predetermined bounds, the sensor provides an alarm to indicate that the viability of the cell is impaired. This is indicated in FIG. 2 by an alarm 50 connected to the A/D Converter section of Analyzer 10 which provides the desired measurement outputs. The levels at which the magnitudes or the variations are judged excessive will depend on the type of cell and its intended application, among other factors, and are readily established in individual cases by those skilled in the art.

Although shown as formed of discrete components, the components comprising the sensor system described herein in practice will desirably be formed in an integrated circuit. This circuit may be integral with the cell itself, that is, incorporated into a single electronic chip mounted within, or on, the electrochemical cell being tested, or may be remote from the cell and connected to it by lead wires, by wireless, or other means; the same is true of the Analyzer chip. Thus, the cell can be continuously monitored during its life and, when the impedance measurements show a decline in viability of the cell of sufficient magnitude, a warning to the user may automatically be provided by the system, thus precluding potential inadvertent reliance on erroneous measurements. The specific conditions under which the warning is generated may, of course, depend on the particular type of cell being monitored as well as the preference of the user. Further, although shown with particular application to a four cell electrode, it will be understood that the sensor circuit of FIG. 2 is also useful in connection with two cell electrodes, in which case the response to the cell drive signals will be taken from the same electrodes as those to which the cell drive signals are applied.

What is claimed is:

1. An apparatus formed on an integrated circuit chip integral with an ion specific electrode comprising:
    a. a signal generator configured to provide AC drive signals over a frequency range;
    b. a signal conditioning unit configured to receive said drive signals and configured to provide, in response thereto, test signals of controlled amplitude and phase to said ion specific electrode;
    c. amplifier circuitry configured to receive from said ion specific electrode response signals responsive to the application of said test signals thereto;
    d. analyzer circuitry configured to receive signals indicative of said test signals and said response signals and configured to provide outputs indicative of a ratio of said signals over said frequency range; and wherein said apparatus forms an integrated circuit chip integral with said ion specific electrode configured to determine the viability of said ion specific electrode.

2. Apparatus according to claim 1 in which said signal conditioning unit provides test signals of equal polarity and opposite phase to said electrode.

3. Apparatus according to claim 2 in which the test signals comprise sinusoidal signals.

4. Apparatus according to claim 3 in which said signal conditioning unit includes current sensing elements for sensing the current drawn from said test signals by the electrode.

5. Apparatus according to claim 4 in which said response signals provide a measure of a voltage created in said electrode responsive to a current applied thereto.

6. Apparatus according to claim 5 in which said analyzer circuitry calculates the ratio of said current and said responsive voltage to provide a measure of the impedance of said electrode.

7. Apparatus according to claim 1 in which said signal conditioning unit includes circuitry for generating an alarm when the viability of the electrode is impaired.

* * * * *